US00PP13364P2

(12) United States Plant Patent
Larsen

(10) Patent No.: US PP13,364 P2
(45) Date of Patent: Dec. 17, 2002

(54) OSTEOSPERMUM PLANT NAMED 'SUNNY DIANA'

(76) Inventor: Bjarne Nyholm Larsen, Grönnegyden 148, DK-5270 Odense N (DK)

( * ) Notice: Subject to any disclaimer, the term of this patent is extended or adjusted under 35 U.S.C. 154(b) by 0 days.

(21) Appl. No.: 10/096,514

(22) Filed: Mar. 12, 2002

(51) Int. Cl.[7] ..... A01H 5/00
(52) U.S. Cl. ..... Plt./360
(58) Field of Search ..... Plt./360

(56) References Cited

U.S. PATENT DOCUMENTS

PP10,996 P * 7/1999 Larsen et al. ..... Plt./360

OTHER PUBLICATIONS

UPOV ROM GTITM Computer Database 2003/02, GTI JOUVE Retrieval Software, Citation(s) for PBR001620.*

* cited by examiner

*Primary Examiner*—Bruce R. Campell
*Assistant Examiner*—W C Baker
(74) *Attorney, Agent, or Firm*—C. A. Whealy

(57) ABSTRACT

A distinct cultivar of Osteospermum plant named 'Sunny Diana', characterized by its upright plant habit; freely branching growth habit; freely flowering habit; and pale yellow-colored ray florets.

2 Drawing Sheets

BOTANICAL CLASSIFICATION/CULTIVAR DESIGNATION

*Osteospermum ecklonis* cultivar Sunny Diana.

BACKGROUND OF THE INVENTION

The present Invention relates to a new and distinct cultivar of Osteospermum plant, botanically known as *Osteospermum ecklonis*, and hereinafter referred to by the name 'Sunny Diana'.

The new Osteospermum is a product of a planned breeding program conducted by the Inventor in Odense, Denmark. The objective of the breeding program is to create new Osteospermum cultivars with attractive ray and disc floret colors.

The new Osteospermum originated from a cross made by the Inventor in May, 1997 of a proprietary selection of *Osteospermum ecklonis* identified as code number 3.44.97, not patented, as the female, or seed, parent with a proprietary selection of *Osteospermum ecklonis* identified as code number 1.44.92, not patented, as the male, or pollen, parent. The new Osteospermum was discovered and selected by the Inventor as a single flowering plant within the progeny of the stated cross grown in a controlled environment in Odense, Denmark in June, 2000.

Asexual reproduction of the new Osteospermum by terminal vegetative cuttings was first conducted in Odense, Denmark in June, 2000. Asexual reproduction by cuttings has shown that the unique features of this new Osteospermum are stable and reproduced true to type in successive generations.

SUMMARY OF THE INVENTION

The cultivar Sunny Diana has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Sunny Diana'. These characteristics in combination distinguish 'Sunny Diana' as a new and distinct Osteospermum:

1. Upright plant habit.
2. Freely branching growth habit.
3. Freely flowering habit.
4. Pale yellow-colored ray florets.

Plants of the new Osteospermum differ from plants of the parents primarily in ray floret color.

Plants of the new Osteospermum can be compared to plants of the cultivar Seidacre, disclosed in U.S. Plant patent application Ser. No. 09/996,362. However, plants of the new Osteospermum are more upright, have larger leaves, have larger inflorescences, and have lighter colored ray florets than plants of the cultivar Seidacre.

BRIEF DESCRIPTION OF THE PHOTOGRAPHS

The accompanying colored photographs illustrate the overall appearance of the new Osteospermum showing the colors as true as it is reasonably possible to obtain in colored reproductions of this type. Colors in the photographs may differ from the color values cited in the detailed botanical description which accurately describe the colors of the new Osteospermum.

The photograph on the first sheet comprises a side perspective view of a typical flowering plant of 'Sunny Diana'.

The photograph on the second sheet is a close-up view of typical inflorescences and leaves of 'Sunny Diana'. The colors in the photograph on the second sheet are closer to the actual colors than the colors in the photograph on the first sheet.

DETAILED BOTANICAL DESCRIPTION

The aforementioned photographs and following observations and measurements describe plants grown in Odense, Denmark, in a glass-covered greenhouse ruing the late spring and early summer with day and night temperatures averaging 20° C. and light levels about 5,000 lux. After planting rooted cuttings, plants were grown for about 13 to 14 weeks in 12-cm containers with one plant per container. Color references are made to The Royal Horticultural Society Colour Chart, 1995 edition, except where general terms of ordinary dictionary significance are used.

Botanical classification: *Osteospermum ecklonis* cultivar Sunny Diana.

Parentage:

*Female, or seed, parent.*—Proprietary selection of *Osteospermum ecklonis* identified as code number 3.44.97, not patented.

*Male, or pollen, parent.*—Proprietary selection of *Osteospermum ecklonis* identified as code number 1.44.92, not patented.

Propagation:

*Type.*—Terminal vegetative cuttings.

*Time to initiate rooting.*—About 10 days at 20° C.

*Time to develop roots.*—About 21 days at 20° C.

*Root description.*—Fine, fibrous and well-branched.

Plant description:

*Appearance.*—Perennial herbaceous container and garden plant. Upright and somewhat outwardly spreading plant habit. Freely branching, about nine to ten lateral branches develop after pinching; dense and full plants. Moderately vigorous growth habit.

*Plant height.*—About 25 cm.

*Plant width or area of spread.*—About 15 cm.

*Lateral branches.*—Length: About 22 cm. Diameter: About 3 mm. Internode length: About 1.25 cm. Aspect: Upright to somewhat outward. Strength: Strong, but flexible. Texture: Pubescent. Color: Close to 143C.

*Foliage description.*—Arrangement: Alternate; simple. Length: About 7 cm. Width: About 2 cm. Shape: Elliptic, strap-like. Apex: Acute. Base: Attenuate. Margin: Entire with occasional tiny serrations. Venation pattern: Pinnate. Texture, upper surface: Rough; glabrous. Texture, lower surface: Slightly rough; glabrous. Color: Young and fully expanded foliage, upper surface: 136A; venation, close to 136A. Young and fully expanded foliage, lower surface: 137C; venation, close to 137C. Petiole: Length: About 1 cm. Diameter: About 5 mm. Texture, upper and lower surfaces: Glabrous. Color, upper and lower surfaces: 144B.

Inflorescence description:

*Appearance.*—Terminal and axillary inflorescences held above and beyond the foliage on moderately strong peduncles. Composite inflorescence form, radially symmetrical; ray and disc florets arranged acropetally on a capitulum. Inflorescences persistent. Inflorescences face upright or outward.

*Flowering response.*—Plants flower continuous and freely from the spring through the fall.

*Postproduction longevity.*—Inflorescences maintain good color and substance for about one week on the plant.

*Quantity of inflorescences.*—Freely flowering; at one time, about ten open inflorescences and inflorescence buds per lateral stem.

*Fragrance.*—None detected.

*Inflorescence bud (at stage of showing color).*—Length: About 1.25 cm. Diameter: About 7.5 mm. Shape: Ovoid. Color, ray florets, lower or outer surface: 4D.

*Inflorescence size.*—Diameter: About 7.5 cm. Depth (height): About 2 cm. Disc diameter: About 1 cm.

*Ray florets.*—Length: About 3.75 cm. Width: About 1 cm. Shape: Ligulate. Apex: Mostly acute. Base: Attenuate. Margin: Entire. Texture, upper and lower surfaces: Smooth, glabrous. Orientation: Initially upright then about 70° from vertical. Number of ray florets per inflorescence: About 21 in a single whorl. Color: When opening and fully opened, upper surface: 4D. When opening and fully opened, lower surface: 4D to 4D; overlain with fine longitudinal stripes, close to 199B to 199C.

*Disc florets.*—Shape: Tubular, elongated. Apex: Five-pointed. Length: About 7.5 mm. Width: At apex: About 1.5 mm. At base: About 1 mm. Number of disc florets per inflorescence: About 52. Color: Immature: Close to 10C; apex, close to 86A. Mature: Close to 1D; apex, close to 83A.

*Phyllaries.*—Length: About 2 cm. Diameter: About 1.5 mm. Shape: Linear. Apex: Narrowly acute. Base: Fused. Margin: Entire. Texture, upper and lower surfaces: Coarse, pubescent. Number per inflorescence: About 21 in a single whorl. Color: Upper surface: 146A. Lower surface: 146C.

*Peduncles.*—Length, terminal peduncle: About 6 cm. Diameter: About 2 mm. Angle: Erect. Strength: Strong. Texture: Pubescent. Color: 146B.

*Reproductive organs.*—Androecium: Present on disc florets only. Stamen number : Five per floret; fused around style. Anther shape: Oblong. Anther length: About 1 mm. Anther color: 95B. Pollen amount: Moderate. Pollen color: Close to 23A. Gynoecium: Present on both ray and disc florets. Pistil number: One per floret. Pistil length: About 7.5 mm. Stigma shape: Two-parted. Stigma color: Close to 83A. Style length: About 5 mm. Style color: Close to 84C. Ovary color: Close to 145A.

*Seed/fruit.*—Seed and/or fruit production has not been observed.

Disease/pest resistance: Resistance to pathogens and pests common to Osteospermums has not been observed on plants grown under commercial greenhouse or outdoor conditions.

Temperature tolerance: Plants of the new Osteospermum have been observed to tolerate temperatures from 1 to more than 35° C.

It is claimed:

1. A new and distinct cultivar of Osteospermum plant named 'Sunny Diana', as illustrated and described.

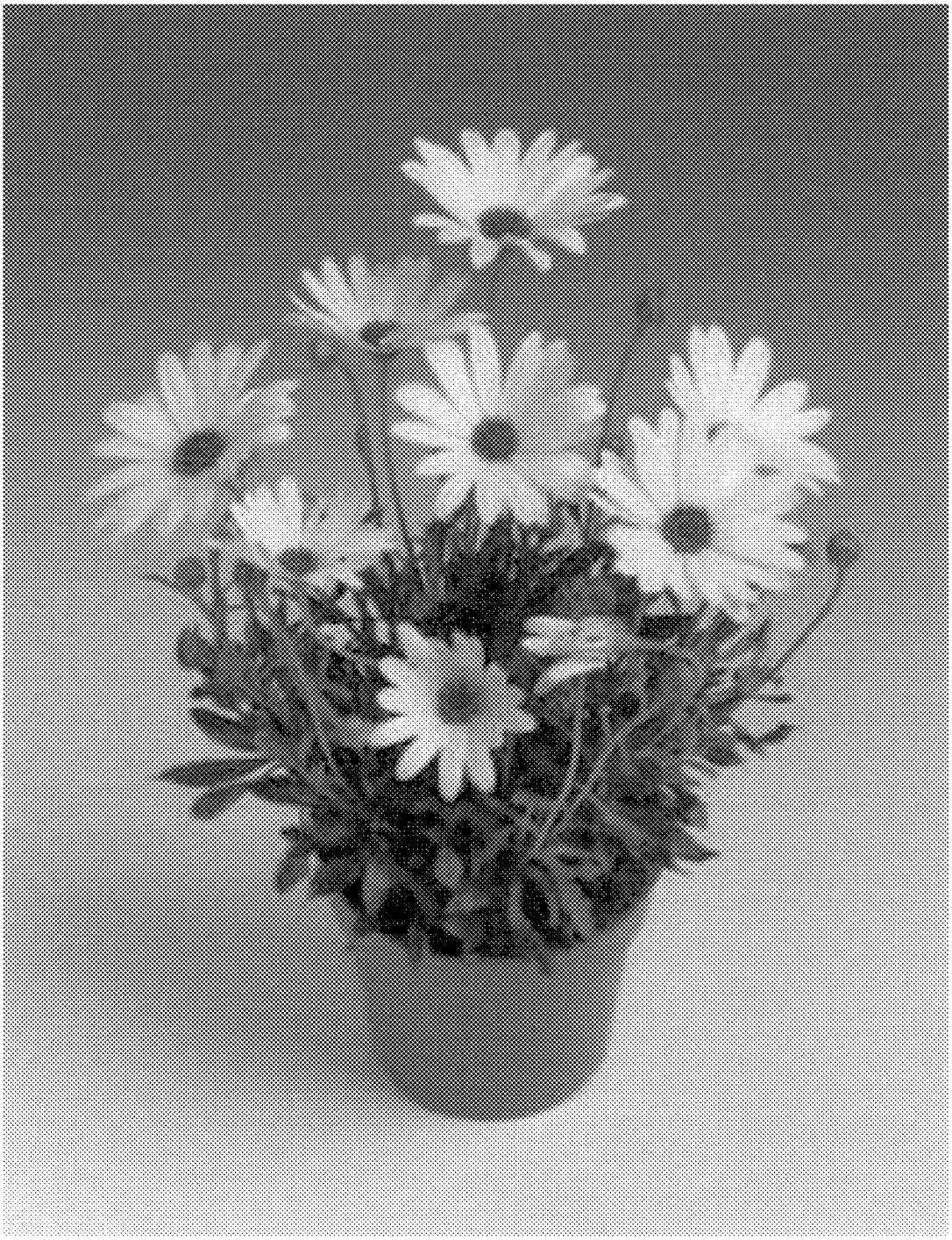

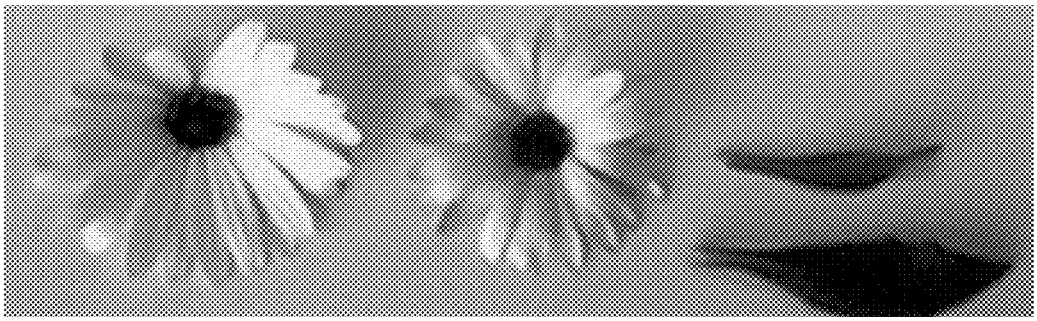

* * * * *